US00PP10872P

United States Patent [19]

Zaiger et al.

[11] Patent Number: Plant 10,872

[45] Date of Patent: Apr. 27, 1999

[54] PEACH TREE NAMED 'KLONDIKE WHITE'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 08/982,135

[22] Filed: Dec. 1, 1997

[51] Int. Cl.[6] ..... A01H 5/00

[52] U.S. Cl. ..... Plt./196

[58] Field of Search ..... Plt./42.1, 196

*Primary Examiner*—Howard J. Locker
*Assistant Examiner*—Anne Marie Grünberg

[57] ABSTRACT

A new and distinct variety of peach tree (*Prunus persica*) which has the following unique combination of desirable features that are outstanding in a new variety. The following features of the tree and its fruit are characterized with the tree budded on nemaguard rootstock, grown on Hanford sandy loam soil with Storie Index rating 95, in USDA hardiness zone 9, near Modesto, Calif., and with standard commercial cultural fruit growing practices, such as, pruning, thinning, spraying, irrigation, fertilization, etc.:

1. Heavy and regular production of large size fruit.
2. Fruit with a mild, sweet, sub-acid flavor and excellent eating quality.
3. Fruit with firm white flesh, good handling and shipping quality.
4. Relatively uniform large-sized fruit throughout the tree.
5. Fruit with a high degree of attractive red skin color.
6. The fruit holding firm on the tree 7 to 10 days after maturity (shipping ripe).

1 Drawing Sheet

ORIGIN OF THE VARIETY

The present new and distinct variety of peach tree was developed by us in our experimental orchard located near Modesto, Calif. as a first generation cross between a selected seedling (field identification number 37G890) and May Crest Peach (U.S. Plant Pat. No. 4,064). The female parent (37G890) originated from a cross of Ruby Gold Nectarine (U.S. Plant Pat. No. 3,101) with a white peach of unknown parentage. A large number of these first generation seedlings growing on their own root were planted and maintained under close observation, during which time one such seedling evidenced desirable tree and fruit characteristics was selected for asexual propagation and commercialization.

ASEXUAL REPRODUCTION OF THE VARIETY

Asexual reproduction of the new and distinct variety of peach tree was by budding on nemaguard rootstock, as performed by us in our experimental orchard located near Modesto, Calif., and shows that all characteristics of the tree and its fruit run true to the original tree and are established and transmitted through succeeding asexual propagations.

SUMMARY OF THE VARIETY

The new and distinct variety of peach tree which is of large size, vigorous, upright growth; and a productive and regular bearer of large size, white flesh, freestone fruit. The firm flesh of the fruit is mild, sweet, sub-acid, with excellent flavor and eating quality, further characterized to its novelty is its relatively uniform size fruit throughout the tree, its good handling and shipping quality, having attractive red skin color and, in comparison to Giant Babcock Peach (U.S. Plant Pat. No. 1,353), the fruit of the new variety has firmer flesh, greater handling and shipping quality and is approximately 2 weeks earlier in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large — tree height controlled by selective pruning to 12 to 14 feet in height and 12 feet to 14 feet in width primarily for economical harvesting.

*Vigor.*—Vigorous — grows 6 to 8 feet in height the first growing season. During first dormant season the tree is pruned to 4 to 5 feet in height and primary scaffolds are selected that will carry a heavy crop load. Height and width of tree is controlled by pruning, primarily in the dormant season.

*Form.*—Usually pruned to vase shape.

*Productivity.*—Productive — fruit set is 1½ or more times the amount desirable for normal tree crop load.

*Bearer.*—Regular — each year fruit must be thinned and spaced to reduce crop load to the number that will make desirable market size fruit. Number of fruit desired per tree varies with age of tree, tree spacing, cultural practices, soil type and climatic conditions.

*Density.*—Medium dense — shoot growth and leaves restrict sunlight and air movement in the center of the tree. The tree is pruned to a vase shape allowing more sunlight and air movement which enhances skin color and fruit with higher Brix.

*Growth.*—Upright.

*Hardiness.*—Winter chilling requirement is approximately 850 hours below 45° F. Hardiness tested only in USDA Hardiness Zone 9.

Trunk:

*Size.*—Medium.

*Texture.*—Medium shaggy.

*Color.*—Mouse gray to soot brown (5-E-5) to (5-F-4).

Branches:

*Size.*—Medium.

*Texture.*—Smooth to medium rough, varies with age of growth.

*Lenticels.*—Numerous. Medium size.

*Color.*—Light brown to brown (5-D-6) to (5-E-4), varies with age of growth.

Leaves:

*Size.*—Large. Average length 6". Average width 1½".

*Form.*—Lanceolate. Pointed.

*Margin.*—Crenate.

*Thickness.*—Medium.

*Surface.*—Slightly crinkled, new leaves somewhat smoother.

*Petiole.*—Medium length — ½". Medium thickness.

*Glands.*—Globose. Number varies from 1 to 4. Average number 2. Medium size. Located on upper portion of petiole and lower portion of leaf blade.

*Color.*—Upper surface — jade green to green (27-E-6) to (27-E-8). Lower surface — dull green to light green (27-E-4) to (27-E-5).

Flower buds:

*Size.*—Large.

*Length.*—Medium.

*Form.*—Plump.

*Pubescence.*—Pubescent.

Flowers:

*Size.*—Large, showy. 1¼" to 1⅜" in diameter.

*Pollen.*—Present, self-fertile.

*Blooming period.*—Date of first bloom: Mar. 4, 1996. Date of last bloom: Mar. 9, 1996. Varies slightly with climatic conditions.

*Color.*—Pink to light pink (10-A-3) to (10-A-2). Pink fades to light pink with age of flowers.

Fruit:

*Maturity when described.*—Firm ripe.

*Date of first picking.*—Jun. 25, 1996.

*Date of last picking.*—Jul. 2, 1996. Varies slightly with climatic conditions.

*Size.*—Large. Average diameter axially 2⅞". Average transversely in suture plane to 3". Average weight 210 grams. Weight varies from 204 to 220 grams.

*Form.*—Nearly globose.

*Suture.*—Shallow, extends from base to apex.

*Ventral surface.*—Rounded.

*Apex.*—Usually rounded, varies from rounded to slight apical tip.

*Base.*—Retuse.

*Cavity.*—Rounded to slightly elongated in suture plane. Average depth ½". Average breadth ¾".

Flesh:

*Ripens.*—Evenly.

*Texture.*—Firm.

*Fibers.*—Small, tender.

*Aroma.*—Slight.

*Amygdalin.*—Undetected.

*Eating quality.*—Excellent.

*Flavor.*—Excellent, mild, sweet, sub-acid.

*Juice.*—Moderate amount — mild, sub-acid, enhances flavor. Average Brix 11.5°. Brix varies with amount of crop load on the tree and climatic conditions — warm temperatures and sunlight increases Brix.

*Color.*—White to yellowish white (1-A-1) to (1-A-2). Pit cavity — greenish white to grayish yellow (1-B-3) to (1-B-4). Very slight bleeding of light red from pit cavity into flesh.

Stem:

*Size.—Medium. Average length* ½". Average diameter ⅛". Enlarged at point of fruit attachment.

*Color.*—Yellowish green to grayish green (1-B-5) to (1-C-5).

Skin:

*Thickness.*—Medium.

*Texture.*—Medium, tenacious to the flesh.

*Down.*—Moderate, short in length.

*Tendency to crack.*—None.

*Color.*—Yellowish white to pastel yellow ground color (1-A-3) to (2-A-4). Overspread with crayfish red to garnet red (9-D-8) to (10-D-8). Fruit with more exposure to sunlight have a greater degree of enhanced red color.

Stone:

*Type.*—Freestone.

*Size.*—Average length 1½". Average width 1⅛". Average thickness ¾".

*Form.*—Obovoid.

*Base.*—Usually straight, varies from straight to rounded.

*Apex.*—Usually acuminate, varies from acuminate to rounded.

*Surface.*—Furrowed toward apex, pitted toward base, both pits and furrows relatively deep. Pits vary from round to elongated. Ridges relatively wide at surface of stone.

*Sides.*—Unequal. One half of the stone is slightly larger in size, extending farther from the suture line, with slightly deeper furrows and pit cavities.

*Tendency to split.*—None.

*Color.*—Light brown to brown (6-D-4) to (6-D-6).

Use: Dessert. Market, local and long distance.

Keeping quality: Good — flesh texture remains firm after 10 days in cold storage.

Shipping quality: Good — minimal bruishing of flesh or skin scarring during picking and shipping trials.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous, upright growth; and a productive and regular bearer of large, firm, white flesh, freestone fruit with good handling and shipping quality; the fruit is further characterized by having a mild, sweet, sub-acid taste with excellent flavor and eating quality, having a high degree of attractive red skin color and, in comparison to the Giant Babcock Peach (U.S. Plant Pat. No. 1,353), the new variety has firmer flesh with greater shipping quality and is approximately 2 weeks earlier in maturity.

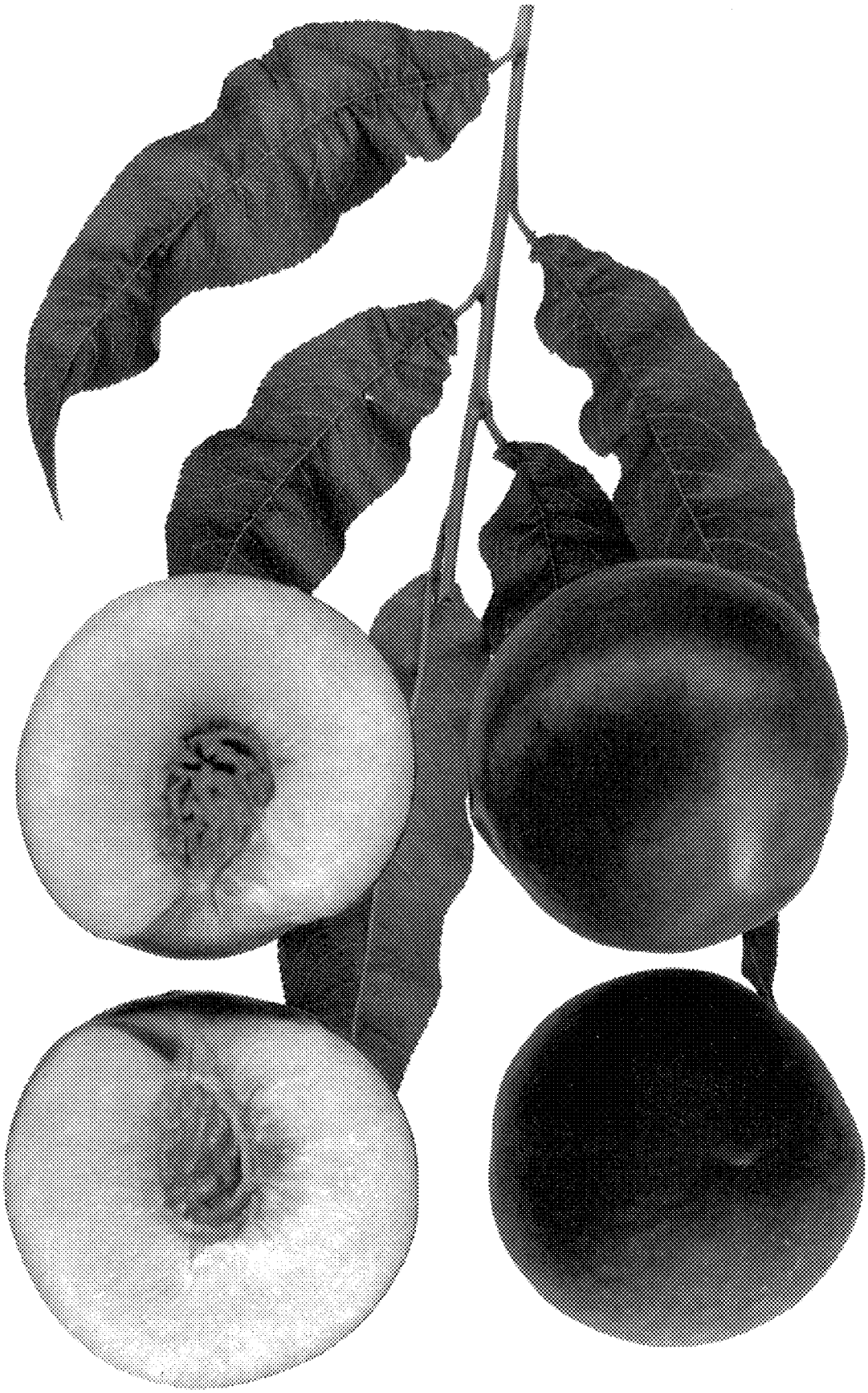

* * * * *